United States Patent [19]

Barnoud et al.

[11] 4,367,647
[45] Jan. 11, 1983

[54] STATIC PENETROMETER

[76] Inventors: François Barnoud, 12 Rue Chancelier-de-l'Hospital, Dijon (Cote-d'Or); Jean-Bernard Labays, Saint-Martin-sous-Montaigu, (Saone-&-Loire), both of France

[21] Appl. No.: 226,405

[22] Filed: Jan. 19, 1981

[30] Foreign Application Priority Data

Jan. 18, 1980 [FR] France ............ 80 01557

[51] Int. Cl.³ ................................. G01N 3/42
[52] U.S. Cl. .............................................. 73/84
[58] Field of Search .......................... 73/84, 81, 784

[56] References Cited

U.S. PATENT DOCUMENTS

| 3,872,717 | 3/1975 | Fox | 73/84 |
| 3,906,781 | 9/1975 | Vlasblom | 73/84 |
| 3,961,524 | 6/1976 | de la Cruz | |
| 4,043,186 | 8/1977 | Marchetti | 73/84 |

FOREIGN PATENT DOCUMENTS

| 568912 | 1/1933 | Fed. Rep. of Germany . |
| 1587397 | 2/1970 | France . |
| 2425650 | 12/1979 | France . |
| 704290 | 2/1954 | United Kingdom . |

Primary Examiner—Herbert Goldstein
Attorney, Agent, or Firm—Karl F. Ross

[57] ABSTRACT

A drill string is provided at its lower end with a downwardly directed point having an upright cylindrical outer surface and a bore opening at this surface. A rod is provided in the bore and has a rod end horizontally displaceable therein between an inner position generally flush with the surface and an outer position spaced horizontally outwardly from the surface. In the inner position the point can be driven or drilled down into the ground. A fluid cylinder in the point has a piston connected to the rod that can be pressurized to urge the rod from the inner to the outer position. Thus the position of the rod end relative to the surface can be detected and the pressure exerted horizontally back against the rod end when it is urged outwardly by the pressurizing means can also be determined to establish the penetration resistance of the ground surrounding the point.

9 Claims, 5 Drawing Figures

STATIC PENETROMETER

FIELD OF THE INVENTION

The present invention relates to a static penetrometer. More particularly this invention concerns a device for determining the static penetration resistance of subsurface soil.

BACKGROUND OF THE INVENTION

A penetration test determines the relative values of density of the ground or soil in bore holes. A standard penetration test is made by determining the number of blows required by a standard weight dropped from a standard height to produce a standard penetration of 12 inches. A dynamic penetration test determines the relative density by recording the penetration per blow or for a specified number of blows. A static penetration test, on the contrary, pushes the testing device into the soil with a measurable force.

Normally this is accomplished simply by exerting the force downwardly on the top end of a drill string at whose bottom end is provided a standard point. In order to measure the static penetration resistance it is necessary to oppose this downward force with an enormous opposite force, normally by providing extremely secure anchors for the apparatus, or having the apparatus work from an extremely large—15-18 tons—piece of equipment. The amount of force necessary to move the entire drill string, in addition, somewhat falsifies the results given by such a test, as the lower end of the drill string might be in relatively soft ground but the overall resistance to displacement along the whole string might be high, giving a falsely high reading.

OBJECTS OF THE INVENTION

It is therefore an object of the present invention to provide an improved static penetrometer.

Another object is to provide such a penetrometer which allows a static penetration test to be carried out relatively easily at any depth during driving of a drill string.

SUMMARY OF THE INVENTION

These objects are attained according to the instant invention in a static penetrometer that is used in combination with the drill string. The penetrometer has a downwardly directed point of the conical-cylindrical type at the lower end of the string which has an upright outer surface and a bore opening at this surface. A rod is provided in the bore and has a rod end which is horizontally—not vertically—displaceable between an outer position spaced horizontally outwardly from the side surface of the point and an inner position generally flush with this surface. Thus the point can be driven or drilled down into the ground with the rod in the inner position. A fluid cylinder is provided in the point connected to the rod and can be pressurized so as to urge the rod from the inner to the outer position. Means is connected to the rod and the cylinder for indicating the position of the rod end relative to the surface and the pressure exerted horizontally back against the rod end when same is urged outwardly by the pressurizing means.

The surface area of the end of the rod is relatively small compared to the semicylindrical surface area of the opposite side of the point, so that the reaction forces as the rod is forced horizontally outwardly by the hydraulic or pneumatic cylinder can easily be withstood. Normally a ratio of at least 20:1 exists so that the drill point does not move laterally at all as the rod is extended outwardly. At the same time the system according to the instant invention allows a static penetration test to be made at any level with the same accuracy, no matter how long the drill string extending between the point and the surface monitoring equipment is. Furthermore the inherent compaction below the drill point becomes largely irrelevant to the test. As a result it is possible in a very simple and easy manner to make static penetration tests at a multiplicity of levels as the string is drilled or driven downwardly. One need only briefly stop the drilling or driving operation to pressurize the cylinder and make the necessary static penetration test. As soon as the test is completed the rod can be withdrawn and drilling or driving continued.

According to further features of this invention the rod is directly fixed on a piston horizontally displaceable in a sleeve inside the point, the piston subdividing this sleeve into a pair of compartments. The compartment turned away from the rod is normally hydraulically pressurized to force the rod outwardly. The other compartment may be hydraulically or pneumatically pressurized to return it or may be simply provided with a return spring whose resistance force is known so that it can be subtracted from the resistance read by the device.

It is also possible with the inventive system to rotate the string after making a penetration test at a certain level and to make a new such test. In this manner any possible local differences in penetration resistance can be detected.

The one compartment of the above-described cylinder sleeve is pressurized according to the instant invention hydraulically. Such hydraulic pressurization can ideally be combined with a pneumatic head above the hydraulic fluid so that the height of the interface between the liquid and gas bodies could be read on a position gauge to give an exact reading of where the piston and rod are relative to the point. The displacing medium itself would be measured to determine the piston and rod positions. Normally the pressure would be increased until motion was detected, the pressure reading at the point immediately before when the piston and rod start moving therefore accurately corresponding to the penetration resistance.

With this system it is possible to use the same body of compressed gas in the other compartment to return the piston to its starting position corresponding to the inner position of the rod. Thus a separate conduit from the gas source to the other compartment is provided. In addition the supply conduit for the hydraulic fluid can be surrounded by a pneumatic supply line, which can be pressurized during a penetration test so as to prevent the conduit filled with hydraulic fluid between the position gauge and the point from stretching outwardly and falsifying the reading.

It is also possible according to this invention to detect the pressure in the one compartment by a simple electronic transducer that produces an electrical analog output corresponding to the pressure in the one compartment. The position of the piston and rod can also be read electrically either by means of a simple linear potentiometer carried on the point with a wiper carried on the rod, or by means of a magnet in the rod detected by a bridge-type coil in the point surrounding the rod.

With such a system the return force can be effected by means of a simple helical spring, or the pressurizing medium can be compressed there.

SPECIFIC DESCRIPTION

Figure 1:
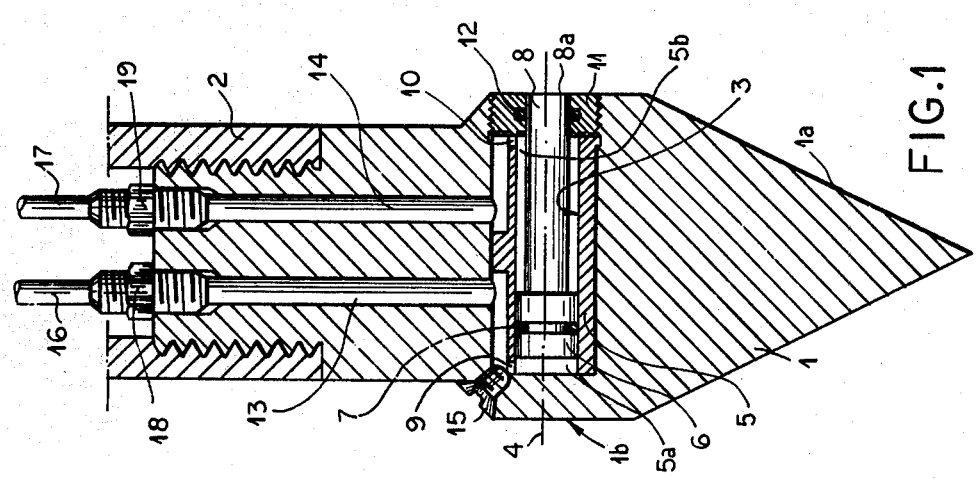
FIG. 1 is an axial section through the penetrometer tip according to this invention.
Figure 2:
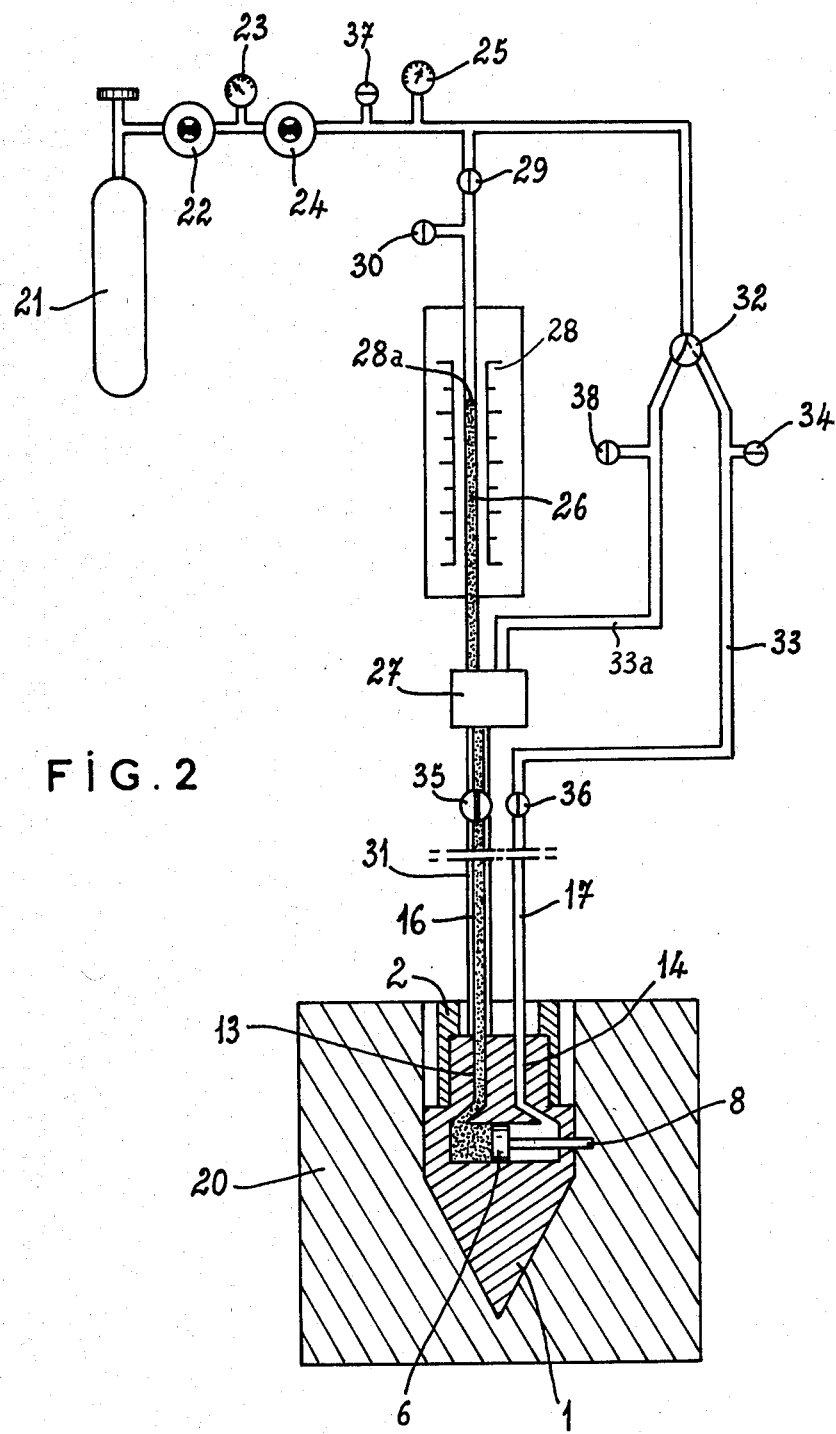
FIG. 2 is a largely schematic view showing a system incorporating the tip of FIG. 1.

As shown in FIGS. 1 and 2 a penetrometer according to this invention has a point 1 having a lower portion with a conical outer surface 1a and an upper portion with a cylindrical outer surface 1b. The point 1 is threaded onto the lower end of a tubular drill string 2 that extends vertically up to above ground.

The point 1 is formed with a horizontally extending blind bore 3 centered on an axis 4 and receiving a cylinder sleeve 5 in which a piston 6 is horizontally axially reciprocable. This piston 6 subdivides the sleeve 5 into a rear compartment 5a and a front compartment 5b. A seal ring 7 prevents fluid flow between the two compartments 5a and 5b. A rod 8 extends axially horizontally away from the piston 6 through the compartment 5b. Holes 9 and 10 through the sleeve 5 open into the compartments 5a and 5b, respectively. A threaded ring 11 provided with a seal 12 holds the sleeve 5 in place inside the bore 3 and has an outer surface forming forming part of the surface 1b, which the end 8a of the rod 8 can lie flush with in the illustrated position.

Passages 13 and 14 communicate via the holes 9 and 10 with the passages 5a and 5b. A bleed screw 15 is threaded into the point 1 to allow the passage 13 and compartment 5a to be bled. Flexible tubes 16 and 17 are connected via fittings 18 and 19 to the upper ends of the passages 13 and 14.

This point 1 is either driven or screwed into the ground 20 in a standard manner. During such driving the piston 6 and rod 8 are in the inner or retracted position shown in FIG. 1.

As shown in FIG. 2 a bottle 21 of compressed gas is connected via a regulating valve 22 to a pressure gauge 23 and then via a fine-adjustment pressure regulating valve 24 to another pressure gauge 25. Then the gas can pass down a clear tube 26 ending at its lower end in a connection 27 from which extends the flexible tube 16. A position gauge 28 is provided along this clear tube 26 so that the interface 28a between the body of gas from the supply 21 and a body of hydraulic fluid indicated by stippling in FIG. 2 can be seen. Obviously as the piston 6 moves the interface 28a will move so as to give an accurate indication of where the piston is.

A bleed valve 30 is provided at the upper end of the tube 26 and another bleed valve 37 between the gauge 25 and valve 24. In addition a valve 29 is provided at the upstream end of the tube 26.

The bottle 21 can also be connected via the pressure-regulating valves 22 and 24 to a three-part valve 32 which can be connected via a line 33 having a bleed valve 34 to the flexible line 17 connected to the compartment 5b. Quick-disconnects 35 and 36 that prevent fluid escape when open are provided in the lines 16 and 17. In addition the valve 32 can connect the bottle 21 to a line 33a extending to the connection 27 to pressurize an outer tube 31 surrounding the tube 16. A bleed valve 38 is provided in the line 33a.

Once the point 1 has been driven to a depth at which a penetration test is to be carried out drilling is stopped and the valve 29 is opened while the valve 32 is switched to pressurize the outer conduit 31 surrounding the conduit 16. Pressure increases and is read on the gauge 25 while the interface 28a is watched. The pressure read on the gauge 25 immediately before the interface 28a starts to move is an indication of the penetration resistance and the position of the interface 28a indicates the volume of the chamber 5a.

After the test the valve 29 is closed, the valve 30 is opened, and the valve 32 is switched to pressurize the compartment 5b via the conduit 33. This forces the piston 6 and rod 8 back into the inner position of FIG. 1.

Figure 3:
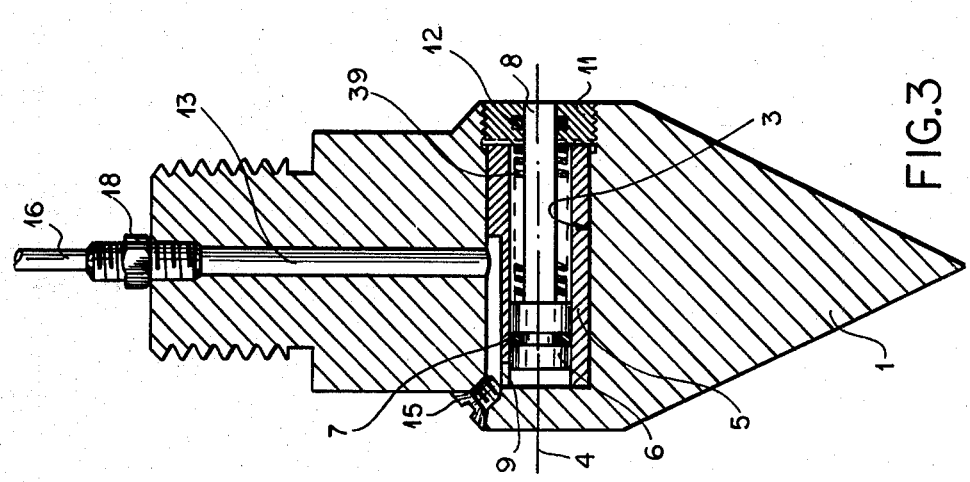

FIG. 3 shows a similar arrangement, but wherein no line 17, fitting 19, and passage 14 are provided. Instead the piston 6 is returned to its inner position by means of a calibrated compression spring 39. Obviously the resistance force of the compression spring 39 must be subtracted from any reading given by this system.

Figure 4:
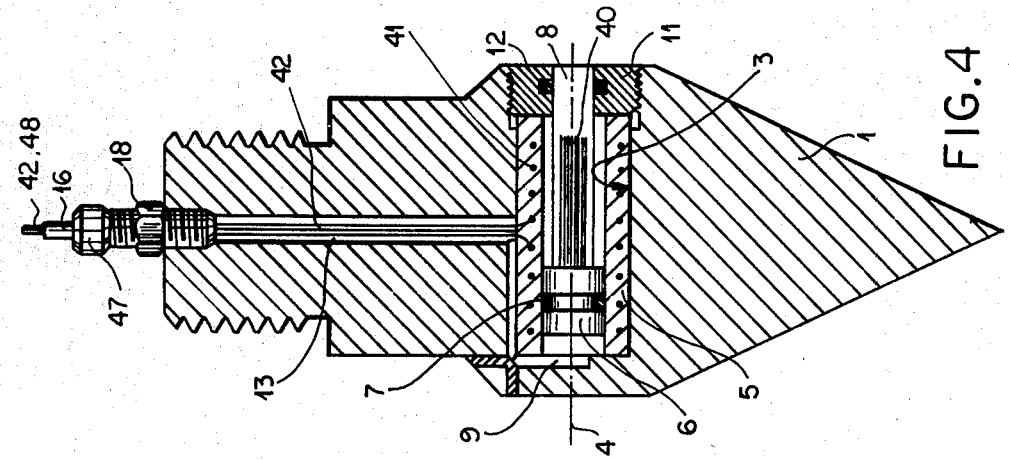
FIGS. 3 and 4 are axial sections through two further penetrometer tips according to the instant invention.
Figure 5:
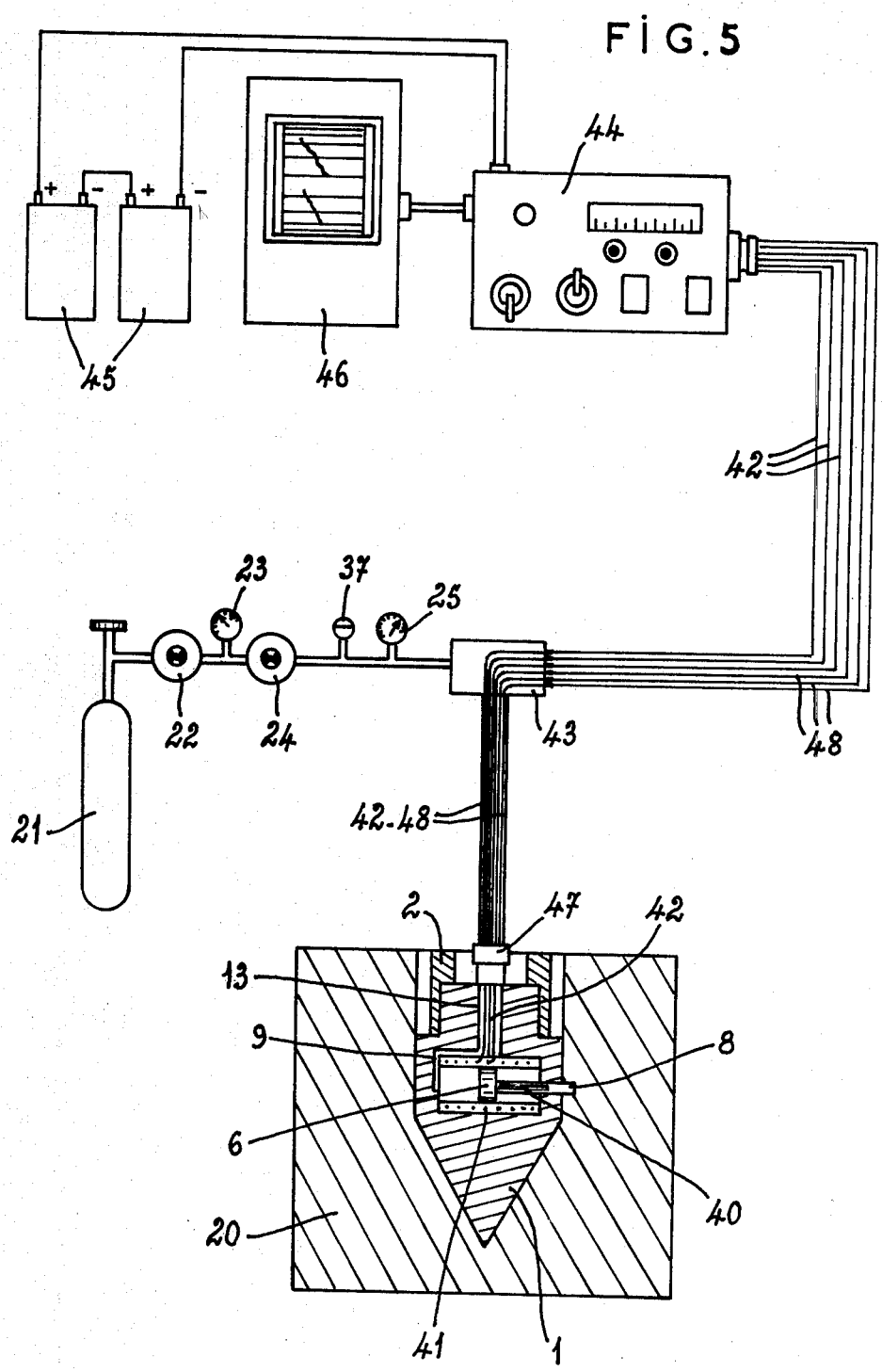
FIG. 5 is a schematic view of a system incorporating the tip of FIG. 4.

FIGS. 4 and 5 show yet another arrangement wherein, once again, piston return is effected by means of a spring 39 or by the simple expedient of applying suction to the input line 16. Here, however, the rod 8 is provided internally with a permanent magnet 40 and a split coil 41 is embedded in the sleeve 5 which is preferably of nonferrous material. The center tap and two ends of the coil 41 are connected to wires 42 which extend up through the conduit 16 and exit therefrom at a connection 43. Then these wires 42 lead to a readout device 44 powered from batteries 45 and connected to a pen scribe 46 that makes a permanent record of the position of the piston 6. The two sides of the coil 41 are connected in a bridge in circuitry inside the unit 44 so that the position of the magnet 40 within the coil 41 can readily be determined.

In addition in accordance with the instant invention the pressure effective on the piston 6 is measured directly at the point 1 by means of an electronic pressure transducer 47 which converts the pressure into an analog electrical output fed via wires 48 to the control unit 45 for entry also by means of the register 46. This system can therefore operate wholly pneumatically and electronically, without the use of hydraulic fluid. Although somewhat more complex, the advantage of not having to connect and disconnect hydraulic lines as sections are added to the string 2 can be considerable.

Thus with the system according to the instant invention it is possible to make a penetration test at virtually any level as a drill point is being driven or screwed into the ground. The test can be carried out with considerable ease and without the use of any heavy equipment. In fact the test can be carried out with such great ease that penetration tests can be made at much more frequent intervals than has hitherto been considered practical, so that an extremely accurate idea of what is being drilled or driven through can be obtained by the operator of the drill.

We claim:

1. A static penetrometer usable in combination with a drill string, said penetrometer comprising:
  a downwardly directed point fixed at the lower end of said string and having a substantially conical lower portion and a substantially cylindrical upper portion, said upper portion having an upright outer surface and a bore opening horizontally at said surface;

a horizontal rod in said bore of said point having a rod end horizontally displaceable in one direction between an outer position spaced horizontally outward from said surface and an inner position generally flush with said surface, whereby said string with said point can be driven or drilled down into the ground with said rod in said inner position to form a hole in which said point fits snugly;

a fluid cylinder in said point connected to said rod;

means for pressurizing said cylinder and urging said rod from said inner to said outer position and thereby pressing said upper portion oppositely to said direction against the side of said hole opposite said rod end; and means connected to said rod and cylinder for indicating the position of said rod end relative to said surface and the pressure exerted horizontally back against said rod end when same is being urged outward by the pressurizing means.

2. The penetrometer defined in claim 1 wherein said cylinder includes a cylinder sleeve and a piston defining two compartments therein, said piston being connected to said rod.

3. The penetrometer defined in claim 2 wherein said means for pressurizing includes a body of hydraulic liquid filling one of said compartments, the other compartment being between said piston and said rod end.

4. The penetrometer defined in claim 1 wherein said indicating means includes and electromagnetic coil in said point adjacent said rod for electrically detecting the position of said rod relative to said point.

5. A static penetrometer usable in combination with a drill string, said penetrometer comprising:

a downwardly directed point at the lower end of said string and having an upright outer surface and a bore opening horizontally at said surface;

a rod in said bore of said point having a rod end horizontally displaceable between an outer position spaced horizontally outward from said surface and an inner position generally flush with said surface, whereby said point can be driven or drilled down into the ground with said rod in said inner position;

a fluid cylinder in said point connected to said rod and including a cylinder sleeve and a piston defining two compartments therein, said piston being connected to said rod;

means for pressurizing said cylinder and thereby urging said rod from said inner to said outer position, the pressurizing means including a body of hydraulic liquid filling one of said compartments, the other compartment being between said piston and said rod end; and means connected to said rod and cylinder for indicating the position of said rod end relative to said surface and the pressure exerted horizontally back against said rod end when same is being urged outward by the pressurizing means, the indicating means including means for measuring the volume and pressure of said liquid in said one compartment.

6. The penetrometer defined in claim 5 wherein said indicating means includes an electronic pressure transducer mounted on said point and serving to convert the pressure of said liquid in said one compartment into an electrical output.

7. The penetrometer defined in claim 5 wherein said pressurizing means includes a body of compressed gas, a gas supply at least partially containing said body, and a conduit provided with a valve and extending between said source and said other compartment for applying the pressure of said gas via said body of hydraulic liquid to said piston.

8. The penetrometer defined in claim 7 wherein said pressurizing means includes a gauge conduit connected between said gas supply and said one compartment and partially containing said body of gas and partially containing said body of liquid, said indicating means including a scale adjacent the interface between said bodies.

9. The penetrometer defined in claim 7 wherein said pressurizing means includes an inner liquid conduit connected between said gas supply and said one compartment and at least partially containing said body of liquid, and outer conduit surrounding said inner conduit, and a valve connected between said outer conduit and said gas supply for pressurizing said outer conduit around said inner conduit.

* * * * *